(12) United States Patent
Nugent et al.

(10) Patent No.: US 8,324,209 B2
(45) Date of Patent: Dec. 4, 2012

(54) PESTICIDAL COMPOSITIONS

(75) Inventors: Benjamin M. Nugent, Brownsburg, IN (US); Zoltan L. Benko, Indianapolis, IN (US); James M. Renga, Indianapolis, IN (US); Michael R. Loso, Carmel, IN (US); Timothy P. Martin, Noblesville, IN (US)

(73) Assignee: Dow AgroSciences, LLC, Indianapolis, IN (US)

( * ) Notice: Subject to any disclaimer, the term of this patent is extended or adjusted under 35 U.S.C. 154(b) by 524 days.

(21) Appl. No.: 12/547,049

(22) Filed: Aug. 25, 2009

(65) Prior Publication Data

US 2010/0056534 A1   Mar. 4, 2010

Related U.S. Application Data

(60) Provisional application No. 61/092,077, filed on Aug. 27, 2008.

(51) Int. Cl.
*A01N 43/48* (2006.01)
(52) U.S. Cl. ............... 514/247; 514/252.01; 514/252.1; 514/255.05; 514/256; 514/269
(58) Field of Classification Search .................. None
See application file for complete search history.

(56) References Cited

U.S. PATENT DOCUMENTS

| 7,511,149 | B2 | 3/2009 | Arndt et al. |
|---|---|---|---|
| 7,541,469 | B2 | 6/2009 | Renga et al. |
| 2005/0228027 | A1 | 10/2005 | Zhu et al. |
| 2007/0203191 | A1 | 8/2007 | Loso et al. |
| 2007/0299264 | A1 | 12/2007 | Huang et al. |
| 2008/0058390 | A1 | 3/2008 | Loso et al. |
| 2008/0108665 | A1 | 5/2008 | Huang et al. |
| 2008/0108666 | A1 | 5/2008 | Loso et al. |
| 2008/0108667 | A1 | 5/2008 | Zhu et al. |
| 2008/0132705 | A1 | 6/2008 | Heller et al. |
| 2008/0194830 | A1 | 8/2008 | Meyer et al. |
| 2008/0280915 | A1 | 11/2008 | Loso et al. |
| 2009/0163720 | A1 | 6/2009 | Renga et al. |

FOREIGN PATENT DOCUMENTS

| WO | WO 96/39389 A1 | 12/1996 |
|---|---|---|
| WO | WO 2006/060029 A2 | 6/2006 |
| WO | W02007/095229 | 8/2007 |
| WO | WO 2007/095229 A2 | 8/2007 |
| WO | WO 2007/149134 A1 | 12/2007 |
| WO | WO 2008/027073 A1 | 3/2008 |
| WO | WO 2008/027539 A1 | 3/2008 |
| WO | WO 2008/057129 A1 | 5/2008 |
| WO | PCT/US2009/054876 | 5/2011 |

*Primary Examiner* — James H. Alstrum-Acevedo
*Assistant Examiner* — Frank Choi
(74) *Attorney, Agent, or Firm* — Carl D. Corvin

(57) ABSTRACT

Pesticide compositions and their use in controlling pests are provided.

11 Claims, No Drawings

PESTICIDAL COMPOSITIONS

This application claims the benefit of U.S. Provisional Application Ser. No. 61/092,077 filed on Aug. 27, 2008. The invention disclosed in this document is related to the field of pesticides and their use in controlling pests.

FIELD OF THE INVENTION

Background of the Invention

Pests cause millions of human deaths around the world each year. Furthermore, there are more than ten thousand species of pests that cause losses in agriculture. These agricultural losses amount to billions of U.S. dollars each year. Termites cause damage to various structures such as homes. These termite damage losses amount to billions of U.S. dollars each year. As a final note, many stored food pests eat and adulterate stored food. These stored food losses amount to billions of U.S. dollars each year, but more importantly, deprive people of needed food.

There is an acute need for new pesticides. Insects are developing resistance to pesticides in current use. Hundreds of insect species are resistant to one or more pesticides. The development of resistance to some of the older pesticides, such as DDT, the carbamates, and the organophosphates, is well known, but resistance has even developed to some of the newer pesticides. Therefore, a need exists for new pesticides and particularly for pesticides that have new modes of action.

SUBSTITUENTS

Non-Exhaustive List

The examples given for the substituents are (except for halo) non-exhaustive and must not be construed as limiting the invention disclosed in this document.

"alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy.

"alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"alkynyloxy" means an alkynyl further consisting of a carbon-oxygen single bond, for example, pentynyloxy, hexynyloxy, heptynyloxy, octynyloxy, nonynyloxy, and decynyloxy.

"aryl" means a cyclic, aromatic substituent consisting of hydrogen and carbon, for example, phenyl, naphthyl, and biphenylyl.

"cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, cycloheptenyl, cyclooctenyl, cyclodecenyl, norbornenyl, bicyclo[2.2.2]octenyl, tetrahydronaphthyl, hexahydronaphthyl, and octahydronaphthyl.

"cycloalkenyloxy" means a cycloalkenyl further consisting of a carbon-oxygen single bond, for example, cyclobutenyloxy, cyclopentenyloxy, cyclohexenyloxy, cycloheptenyloxy, cyclooctenyloxy, cyclodecenyloxy, norbornenyloxy, and bicyclo[2.2.2]octenyloxy.

"cycloalkyl" means a monocyclic or polycyclic, saturated substituent consisting of carbon and hydrogen, for example, cyclopropyl, cyclobutyl, cyclopentyl, cyclohexyl, cycloheptyl, cyclooctyl, cyclodecyl, norbornyl, bicyclo[2.2.2]octyl, and decahydronaphthyl.

"cycloalkoxy" means a cycloalkyl further consisting of a carbon-oxygen single bond, for example, cyclopropyloxy, cyclobutyloxy, cyclopentyloxy, cyclohexyloxy, cycloheptyloxy, cyclooctyloxy, cyclodecyloxy, norbornyloxy, and bicyclo[2.2.2]octyloxy.

"halo" means fluoro, chloro, bromo, and iodo.

"haloalkyl" means an alkyl further consisting of, from one to the maximum possible number of, identical or different, halos, for example, fluoromethyl, difluoromethyl, trifluoromethyl, 1-fluoromethyl, 2-fluoroethyl, 2,2,2-trifluoroethyl, chloromethyl, trichloromethyl, and 1,1,2,2-tetrafluoroethyl.

"heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen, for example, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, 1,3,4-oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, 1,2,3,4-tetrazolyl, thiazolinyl, thiazolyl, thienyl, 1,2,3-triazinyl, 1,2,4-triazinyl, 1,3,5-triazinyl, 1,2,3-triazolyl, and 1,2,4-triazolyl.

DETAILED DESCRIPTION OF THE INVENTION

The pesticidal compositions of this invention comprise a molecule having the following general formula:

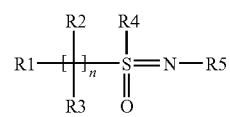

(1)

wherein
R1 is
(a) an unsubstituted pyrimidinyl, pyridazinyl, or pyrazinyl, or
(b) a substituted pyrimidinyl, pyridazinyl or pyrazinyl, wherein each substituted pyrimidinyl, pyridazinyl, or pyrazinyl, has one or more substituents independently selected from $(C_2-C_6)$alkenyl, $(C_2-C_6)$alkenyloxy, $(C_1-C_6)$alkoxy, $(C_1-C_6)$alkyl, $(C_2-C_6)$alkynyl, $(C_2-C_6)$alkynyloxy, aryl, $(C_3-C_6)$cycloalkenyl, $(C_3-C_6)$cycloalkenyloxy, $(C_3-C_6)$cycloalkyl, $(C_3-C_6)$cycloalkoxy, halo, halo $(C_1-C_6)$alkyl, or heterocyclyl;

R2 is H, $(C_2-C_6)$alkenyl, $(C_2-C_6)$alkenyloxy, $(C_1-C_6)$alkoxy, $(C_1-C_6)$alkyl, $(C_2-C_6)$alkynyl, $(C_2-C_6)$alkynyloxy, aryl, $(C_3-C_6)$cycloalkenyl, $(C_3-C_6)$cycloalkenyloxy, $(C_3-C_6)$cycloalkyl, $(C_3-C_6)$cycloalkoxy, halo, halo$(C_1-C_6)$alkyl, or heterocyclyl;

R3 is H, $(C_2-C_6)$alkenyl, $(C_2-C_6)$alkenyloxy, $(C_1-C_6)$alkoxy, $(C_1-C_6)$alkyl, $(C_2-C_6)$alkynyl, $(C_2-C_6)$alkynyloxy, aryl, $(C_3-C_6)$cycloalkenyl, $(C_3-C_6)$cycloalkenyloxy, $(C_3-C_6)$cycloalkyl, $(C_3-C_6)$cycloalkoxy, halo, halo$(C_1-C_6)$alkyl, or heterocyclyl;

Optionally, R2 and R3 may form a ring wherein the ring contains 3 or more ring atoms optionally containing an O, S, or N atom;

R4 is H, $(C_2-C_6)$alkenyl, $(C_2-C_6)$alkenyloxy, $(C_1-C_6)$alkoxy, $(C_1-C_6)$alkyl, $(C_2-C_6)$alkynyl, $(C_2-C_6)$alkynyloxy, aryl, $(C_3-C_6)$cycloalkenyl, $(C_3-C_6)$cycloalkenyloxy, $(C_3-C_6)$cycloalkyl, $(C_3-C_6)$cycloalkoxy, halo, halo$(C_1-C_6)$alkyl, or heterocyclyl;

Optionally, R4 and R2 are joined together to form a 4-, 5-, or 6-membered ring with —(CH$_2$)—;

R5 is NO$_2$, CN, CO$_2$R$_6$, unsubstituted heterocyclyl, substituted heterocyclyl, C(=O or S))J(J1)(J2), wherein the substituted heterocyclyl has one or more substituents that are independently selected from $(C_2-C_6)$alkenyl, $(C_2-C_6)$alkenyloxy, $(C_1-C_6)$alkoxy, $(C_1-C_6)$alkyl, $(C_2-C_6)$alkynyl, $(C_2-C_6)$alkynyloxy, aryl, aryl$(C_1-C_6)$alkyl, $(C_3-C_6)$cycloalkenyl, $(C_3-C_6)$cycloalkenyloxy, $(C_3-C_6)$cycloalkyl, $(C_3-C_6)$cycloalkoxy, halo, halo$(C_1-C_6)$alkyl, heterocyclyl, and wherein J is N or C(J3), and wherein J1, J2, and J3, are independently selected from $(C_2-C_6)$alkenyl, $(C_2-C_6)$alkenyloxy, $(C_2-C_6)$alkenylthio, $(C_1-C_6)$alkoxy, $(C_1-C_6)$alkyl, $(C_1-C_6)$alkylthio, $(C_2-C_6)$alkynyl, $(C_2-C_6)$alkynyloxy, $(C_2-C_6)$alkynylthio, aryl, $(C_3-C_6)$cycloalkenyl, $(C_3-C_6)$cycloalkenyloxy, $(C_3-C_6)$cycloalkenylthio, $(C_3-C_6)$cycloalkyl, $(C_3-C_6)$cycloalkoxy, $(C_3-C_6)$cycloalkylthio, H, heterocyclyl, or $(C_0-C_6)$alkyl-C(=O)O(J4), wherein each of which may be independently substituted (except for H) with one or more of the following substituents, F, Cl, Br, I, CN, NO$_2$, $(C_1-C_6)$alkyl, $(C_2-C_6)$alkenyl, $(C_2-C_6)$alkynyl, $(C_1-C_6)$alkoxy, $(C_1-C_6)$haloalkyl, $(C_1-C_6)$haloalkoxy, halo$(C_1-C_6)$alkylthio, S(=O)$_{n1}$(C1-C$_6$)alkyl (where n1=0-2), S(=O)$_{n2}$ halo$(C_1-C_6)$alkyl (where n2=0-2), OSO$_2$halo(C1-C$_6$)alkyl, C(=O)O(C$_1$-C$_6$)alkyl, C(=O)(C$_1$-C$_6$)alkyl, C(=O)halo$(C_1-C_6)$alkyl, aryl, hydroxy$(C_1-C_6)$alkyl, N(J5)(J6), and heterocyclyl, and wherein J1 and J2 may also form a 4-, 5-, or 6-membered ring, and wherein J4, J5, and J6 are independently selected from $(C_2-C_6)$alkenyl, $(C_2-C_6)$alkenyloxy, $(C_2-C_6)$alkenylthio, $(C_1-C_6)$alkoxy, $(C_1-C_6)$alkyl, $(C_1-C_6)$alkylthio, $(C_2-C_6)$alkynyl, $(C_2-C_6)$alkynyloxy, $(C_2-C_6)$alkynylthio, aryl, $(C_3-C_6)$cycloalkenyl, $(C_3-C_6)$cycloalkenyloxy, $(C_3-C_6)$cycloalkenylthio, $(C_3-C_6)$cycloalkyl, $(C_3-C_6)$cycloalkoxy, $(C_3-C_6)$cycloalkylthio, H, or heterocyclyl, and wherein R6=$(C_1-C_3)$alkyl; and n is 0, 1, 2, or 3.

In another embodiment of the invention, R1 is

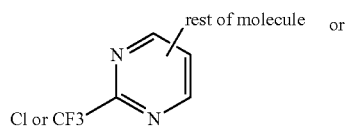

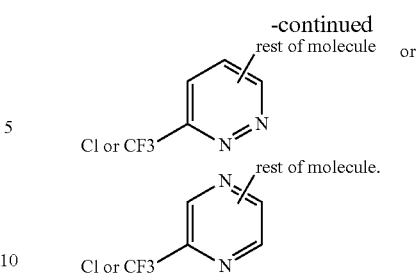

Procedures known in the art can be used to make the molecules herein, In general, these molecules can be made as follows.

The compounds of formula (1a), wherein R$^5$ represents CN and R$^1$, R$^2$, R$^3$, R$^4$ are as previously defined, can be prepared by the method illustrated in Scheme A. The methylene carbon adjacent to the heterocyclic ring R$^1$ is first halogenated using N-bromosuccinimide, N-chlorosuccinimide, or trichloroisocyanuric acid. The sulfide is prepared by nucleophilic substitution of the halide with the sodium salt of an alkyl thiol. The sulfide is oxidized with iodobenzene diacetate in the presence of cyanamide at 0° C. to give the sulfilimine. The reaction can be carried out in a polar aprotic solvent like dichloromethane (CH$_2$Cl$_2$). The sulfilimine is then oxidized with meta-chloroperoxybenzoic acid (mCPBA). A base such as potassium carbonate is employed to neutralize the acidity of mCPBA. Protic polar solvents such as ethanol and water are used to increase the solubility of the sulfilimine starting material and the base employed. The sulfilimine can also be oxidized with aqueous sodium or potassium periodate solution in the presence of a catalyst such as ruthenium trichloride hydrate or similar. The organic solvent for this catalysis can be a polar aprotic solvent such as CH$_2$Cl$_2$, chloroform, or acetonitrile.

Scheme A

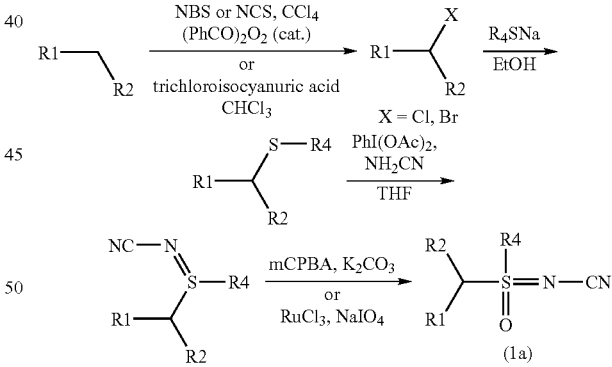

The compounds of formula (1b), wherein R$^1$, R$^2$, R$^3$, R$^4$, are as previously defined and R$^5$ is CN, NO$_2$, or CO$_2$R$_6$, can be prepared from the sulfide by the methods illustrated in Scheme B. The sulfide is oxidized with mCPBA in a polar solvent below 0° C. to provide the sulfoxide. In most cases, CH$_2$Cl$_2$ is a preferred solvent for oxidation. The sulfoxide is then iminated with sodium azide in the presence of concentrated sulfuric acid in an aprotic solvent under heating to provide the sulfoximine. In most cases, chloroform is a preferred solvent for this reaction. The nitrogen of the sulfoximine can be either cyanated with cyanogen bromide in the presence of a base, nitrated with nitric acid in the presence of acetic anhydride under mildly elevated temperature, or carboxylated with an alkyl ($R^6$) chloroformate in the presence of a base such as 4-dimethylaminopyridine (DMAP) to provide the N-substituted sulfoximine. Base is required for efficient cyanation and carboxylation and the preferred base is DMAP, whereas sulfuric acid is used as a catalyst for efficient nitration reaction.

Scheme B

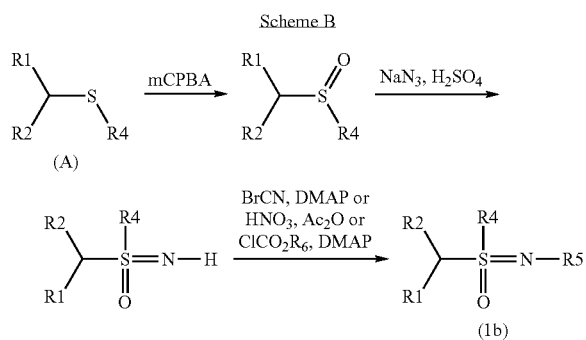

The compounds of formula (1c), wherein $R^1$, $R^2$, $R^3$, $R^4$, are as previously defined and $R^5$ is thiourea (—C(S)NH$_2$), can be prepared from the unsubstituted (N—H) sulfoximine by the methods illustrated in Scheme C. The sulfoximine nitrogen is reacted with Fmoc-isothiocyanate (Fmoc=9-fluorenylmethoxycarbonyl) to furnish the Fmoc-protected thiourea. Deprotection of the thiourea can be achieved through treatment with a base such as piperidine in a solvent such as N,N-dimethylformamide (DMF).

Scheme C

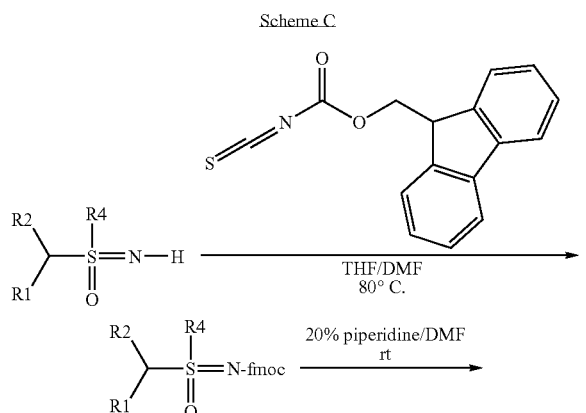

The compounds of formula (1d), wherein $R^1$, $R^2$, $R^3$, $R^4$, are as previously defined and $R^5$ is a substituted or unsubstituted thiazole, can be prepared from the thiourea-substituted sulfoximine (1c) by the method illustrated in Scheme D. Reaction of (1c) with a suitably substituted α-bromoketone or α-bromoaldehyde (where $R^7$ and $R^8$ are independently H, alkyl, haloalkyl, substituted or unsubstituted aryl, or aryl(C$_1$-C$_6$)alkyl) furnishes the N-thiazolyl sulfoximine (1d).

Scheme D

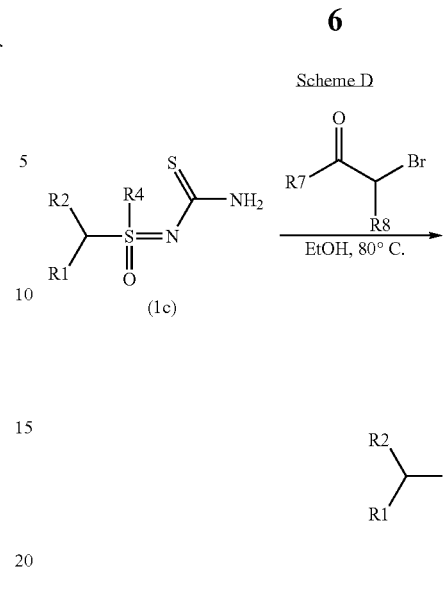

The α-carbon of the N-substituted sulfoximine, where, $R^2$ and $R^3$=H and $R^1$, $R^4$ and $R^5$ are as previously defined, can be further alkylated or halogenated ($R^2$) in the presence of a base such as potassium hexamethyldisilazide (KHMDS) to give N-substituted sulfoximines of formula (1e), wherein $R^1$, $R^4$, $R^5$ are as previously defined and Z is an appropriate leaving group, as illustrated in Scheme E. The preferred leaving groups are iodide (R2=alkyl), benzenesulfonimide (R2=F), tetrachloroethene (R2=Cl), and tetrafluoroethene (R2=Br).

Scheme E

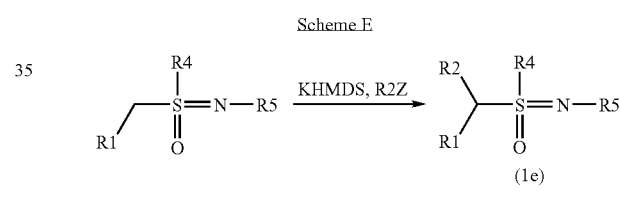

In Scheme F, the sulfide of formula (A$_1$) can be prepared from the corresponding substituted chloromethyl heterocyclyl by treatment with thiourea, hydrolysis and subsequent alkylation with the appropriate bromo chloroalkane (m=0, 1, or 2) under aqueous base conditions, and cyclization in the presence of a base like potassium-t-butoxide in a polar aprotic solvent such as tetrahydrofuran (THF).

Scheme F

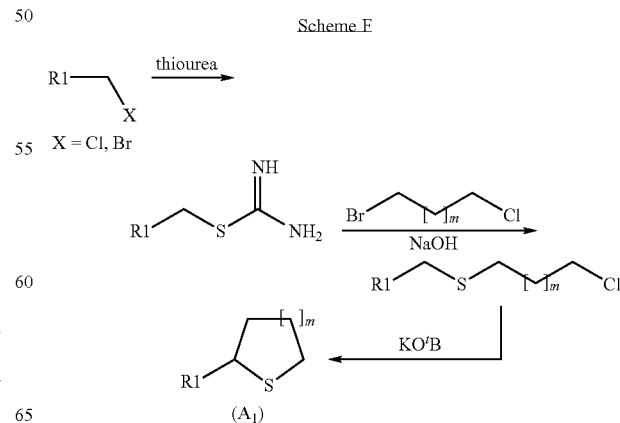

Sulfoximine compounds of the formula (If) wherein n=2, $R^2$ and $R^3$ are hydrogen and $R^1$, $R^4$ and $R^5$ are as previously defined, can be prepared by the method illustrated in Scheme G. Dimethylsulfide is oxidized with iodobenzene diacetate in the presence of cyanamide at 0° C. to give the corresponding sulfilimine. The reaction can be carried out in a polar aprotic solvent like $CH_2Cl_2$ or THF. The sulfilimine is then oxidized with mCPBA. A base such as potassium carbonate is employed to neutralize the acidity of mCPBA. Protic polar solvents such as ethanol and water are used to increase the solubility of the sulfilimine starting material and the base employed. The α-carbon of the N-substituted sulfoximine can be alkylated with a heteroaromatic methyl halide in the presence of a base such as KHMDS or butyl lithium (nBuLi) to give the desired N-substituted sulfoximine. The preferred halide can be bromide, chloride or iodide.

Scheme G

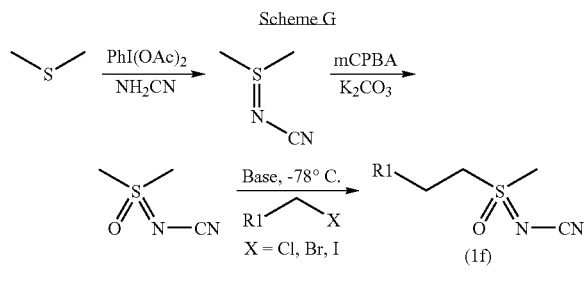

Sulfide compounds of the formula ($A_2$) can be prepared by the method illustrated in Scheme H. 2-Ethoxymethylenemalonic acid diethyl ester is reacted with trifluoroacetamidine to form a pyrimidinone, which can then be chlorinated with oxalyl chloride. The chloropyrimidine can be reduced using hydrogen and a palladium on carbon catalyst to give the corresponding pyrimidine. The ester can then be reduced to the aldehyde using diisobutylaluminum hydride (DIBAL-H) which can then be alkylated with a Grignard reagent ($R_2MgBr$). The resulting alcohol can be chlorinated using thionyl chloride, and then nucleophilic substitution of the halide with the sodium salt of an alkyl thiol will furnish the desired sulfide.

Scheme H

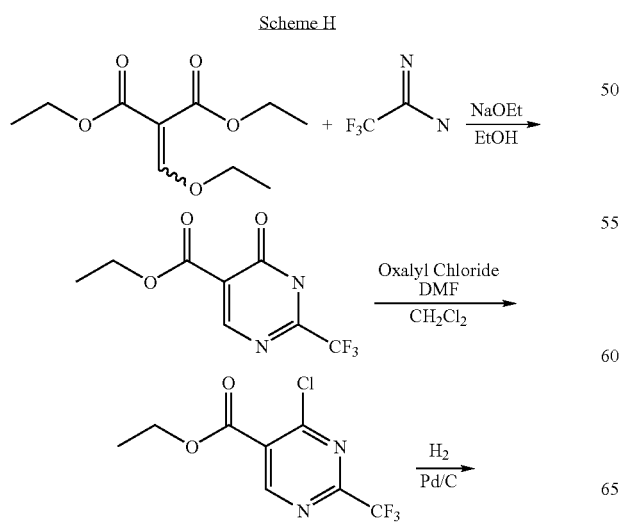

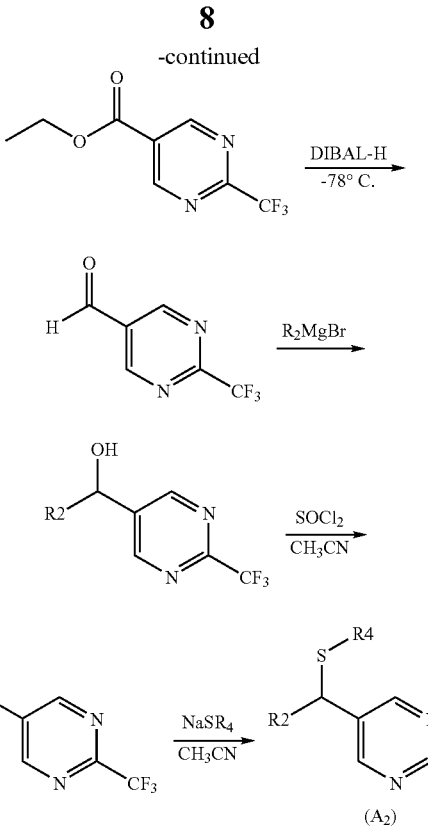

EXAMPLES

The examples are for illustration purposes and are not to be construed as limiting the invention disclosed in this document to only the embodiments disclosed in these examples.

Example I

Preparation of [1-(2-chloropyrimidin-5-yl)ethyl](methyl)oxido-$\lambda^4$-sulfanylidenecyanamide (1)

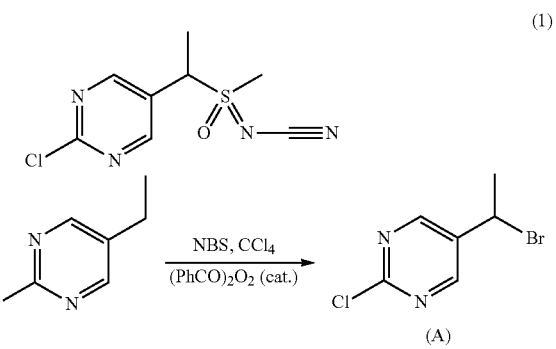

A solution of 2-chloro-5-ethylpyrimidine (1.15 g, 8.1 mmol) in 20 mL of carbon tetrachloride was treated with N-bromosuccinimide (1.50 g, 8.4 mmol) and a catalytic amount (about 1 mol percent based on reactants) of benzoyl peroxide and then heated to 75° C. After several hours and additional catalyst, the starting material was completely consumed. The solids were removed and the filtrate was concentrated. The resulting residue was further purified by flash column chromatography on silica gel using a mixture of ethyl acetate (EtOAc) and petroleum ether as the eluant. The solvents were removed under reduced pressure to yield 0.64 g (36%) of 5-(1-bromoethyl)-2-chloropyrimidine (A) as a clear liquid: $^1$H NMR (CDCl$_3$) δ 8.70 (s, 2H), 5.15 (q, J=8.0 Hz, 1H), 2.10 (d, J=8.0 Hz, 3H); GCMS (FID) m/z 222 (M+). Some of the corresponding dibromo compound 0.44 g (18%) was also isolated, as a white solid: mp 84-85° C.; $^1$H NMR (CDCl$_3$) d 9.00 (s, 2H), 3.00 (s, 3H); LC-MS (ESIMS) m/z 298 (M+H).

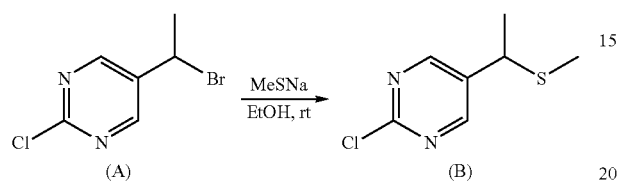

A suspension of sodium methylthiolate (245 mg, 3.50 mmol) in ethanol was treated with a solution of 5-(1-bromoethyl)-2-chloropyrimidine in ethanol at room temperature. After 5 hours (h), the reaction was partitioned between CH$_2$Cl$_2$ and dilute hydrochloric acid, washed with saturated brine and dried over sodium sulfate (Na$_2$SO$_4$). The solvent were removed under reduced pressure to yield 0.45 g (89%) of 2-chloro-5-[1-(methylthio)ethyl]pyrimidine (B) as a pale yellow syrup: $^1$H NMR (CDCl$_3$) δ 8.60 (s, 2H), 3.85 (q, J=8.0 Hz, 1H), 1.98 (s, 3H), 1.65 (d, J=8.0 Hz, 3H); GC-MS (FID) m/z 188 (M+).

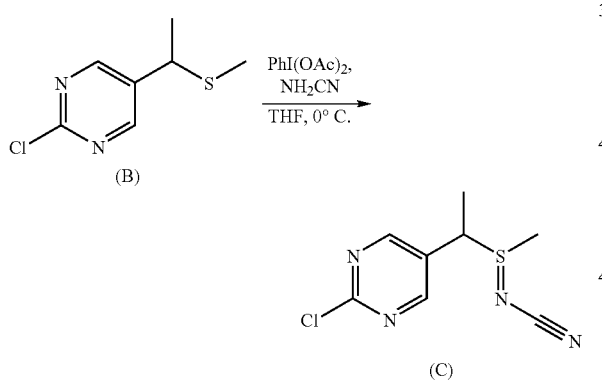

A solution of 2-chloro-5-[1-(methylthio)ethyl]pyrimidine (0.49 g, 2.61 mmol) and cyanamide (120 mg, 2.86 mmol) in 20 mL of CH$_2$Cl$_2$ was cooled to 0° C. and treated with iodobenzene diacetate (860 mg, 2.59 mmol). The mixture was allowed to warm to room temperature over an hour, the solvent was removed under reduced pressure and the residue was partitioned between hexanes and acetonitrile. The acetonitrile was removed under reduced pressure and the residue was further purified by flash column chromatography on silica gel using a 50% mixture of acetone and petroleum ether as the eluant. The solvents were removed under reduced pressure to yield 0.44 g (74%) of (1E)-[1-(2-chloropyrimidin-5-yl)ethyl](methyl)-λ$^4$-sulfanylidenecyanamide (C) as a pale orange syrup. This material was a 2:1 mixture of diastereomers. The physical properties of the major diastereomer were: $^1$H NMR (CDCl$_3$) δ 8.68 (s, 2H), 4.38 (q, J=8.3 Hz, 1H), 2.68 (s, 3H), 1.92 (d, J=8.3 Hz, 3H); LC-MS (ESI) m/z 229 (M+H).

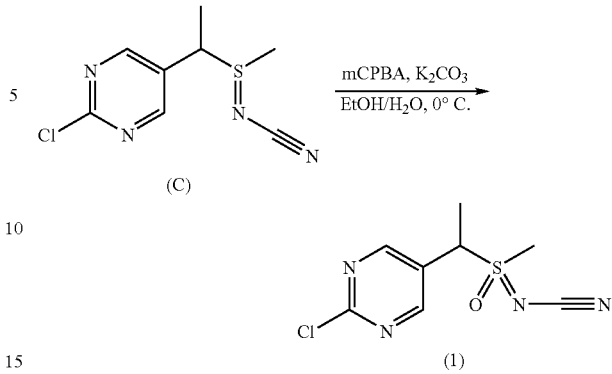

A rapidly stirring mixture of sodium periodate (458 mg, 2.14 mmol) in 10 mL of a 1:1 mixture of water (H$_2$O) and CH$_2$Cl$_2$ was first treated with ruthenium(III) chloride hydrate (13 mg, 0.06 mmol) and then a solution of (1E)-[1-(2-chloropyrimidin-5-yl)ethyl](methyl)-λ$^4$-sulfanylidenecyanamide (242 mg, 1.06 mmol) in 7 mL of CH$_2$Cl$_2$ added dropwise over 15 min. The mixture was stirred for 18 h at room temperature. The dark mixture was then partitioned between CH$_2$Cl$_2$ and dilute hydrochloric acid, and the organic layer was dried over Na$_2$SO$_4$. The solvent was removed under reduced pressure, and the residue was taken up in acetone and passed through a plug of alumina. The acetone was removed under reduced pressure to yield 122 mg (50%) of [1-(2-chloropyrimidin-5-yl)ethyl](methyl)oxido-λ$^4$-sulfanylidenecyanamide (1) as a clear syrup. This material was a 2:1 mixture of diastereomers. The physical properties of the major diastereomer were: $^1$H NMR (CDCl$_3$) δ 8.68 (s, 2H), 4.52 (q, J=9 Hz, 1H), 3.10 (s, 3H), 1.95 (d, J=9 Hz, 3H); LC-MS (ESI) m/z 245 (M+H).

Example II

Preparation of [(3-chloropyridazin-6-yl)methyl](methyl)oxido-λ$^4$-sulfanylidenecyanamide (2)

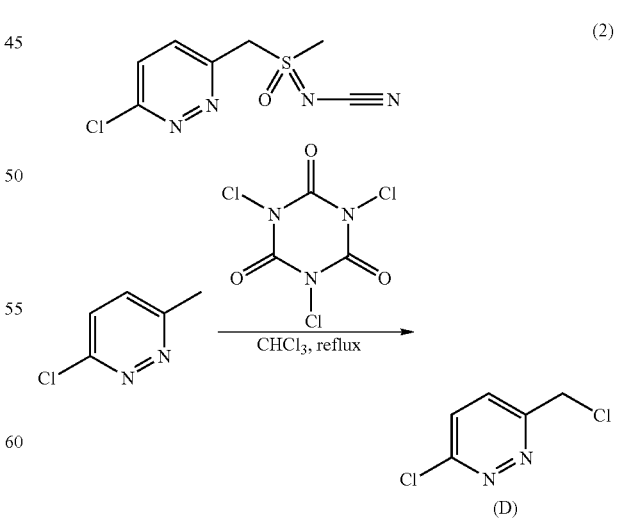

To a refluxing solution of 3-chloro-6-methylpyridazine (5.0 g, 39 mmol) in chloroform (75 mL) was added trichloroisocyanuric acid (3.6 g, 16 mmol) portionwise. The solution was allowed to reflux overnight, after which the crude reaction mixture was filtered, washed with 1 M sodium hydroxide (NaOH), and the organic phase was dried over magnesium sulfate. The crude product was concentrated under reduced pressure and purified by silica gel chromatography to furnish 3-chloro-6-chloromethyl-pyridazine (D) as a yellow oil which upon sitting became a brown solid=2.9 g (46%).

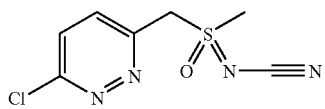

(2)

[(3-Chloropyridazin-6-yl)methyl](methyl)oxido-$\lambda^4$-sulfanylidenecyanamide (2) was synthesized from 3-chloro-6-chloromethyl-pyridazine (D) using the synthetic procedure provided in Example I. The desired product was isolated as a yellow solid: $^1$H NMR (CDCl$_3$) δ 7.3 (d, J=7.5 Hz, 1H), 7.2 (d, J=7.5 Hz, 1H) 4.8 (m, 2H), 2.8 (s, 3H); LC-MS (ESI) m/z 230 (M+).

Example III

Preparation of methyl(oxido){1-[2-(trifluoromethyl)pyrimidin-5-yl]ethyl}-$\lambda^4$-sulfanylidenecyanamide (3)

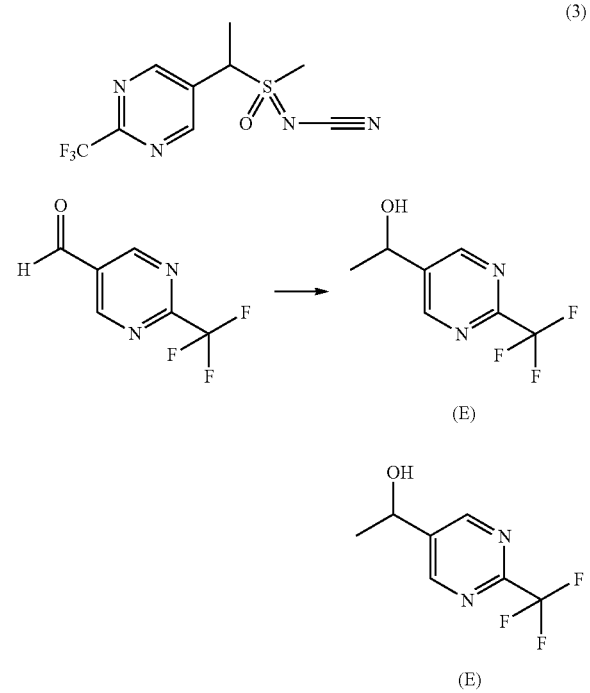

To a magnetically stirred solution of methyl Grignard (19.9 mL of a 3 M solution in ether (Et$_2$O), 59.7 mmol) in Et$_2$O (167 mL) was added a solution of 2-trifluoromethylpyrimidine-5-carbaldehyde (9.56 g, 54.3 mmol) in Et$_2$O (50 mL) at 0° C., and the resulting pale yellow solution was warmed to room temperature (RT) and stirred for 2.5 h. The reaction was quenched by the addition of saturated aqueous ammonium chloride (NH$_4$Cl) (50 mL) at 0° C., and the mixture was warmed to RT. The phases were separated and the organic phase was dried over Na$_2$SO$_4$, filtered, and concentrated to give a light yellow oil (9.32 g crude). The oil was purified by flash chromatography (330 g SiO$_2$, 0→100% EtOAc/hexanes gradient) to give 1-(2-trifluoromethylpyrimidin-5-yl)ethanol (E) (8.87 g, 85%) as a light yellow solid: mp 43-45° C.; $^1$H NMR (300 MHz, CDCl$_3$) δ 8.92 (s, 2H), 5.15-5.07 (m, 1H), 2.26 (d, J=4.0 Hz, 1H), 1.62 (d, J=6.5 Hz, 3H); MS (EI) m/z 192 (M)$^+$.

*2-Trifluoromethylpyrimidine-5-carbaldehyde can be prepared in four steps through methods known in the literature.

1) Fenwick, A. E.; Hickey, D. M. B.; Ife, R. J.; Leach, C. A.; Pinto, I. L.; Smith, S. A. (SmithKline Beecham PLC, UK). WO 200066567, Nov. 9, 2000.

2) Hickey, D. M. B.; Ife, R. J.; Leach, C. A.; Smith, S. A. (SmithKline Beecham PLC, UK). WO 200066566, Nov. 9, 2000.

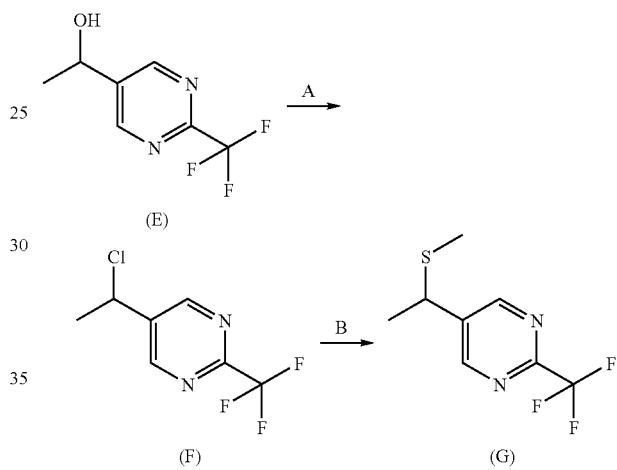

A) To a magnetically stirred solution of 1-(2-trifluoromethylpyrimidin-5-yl)ethanol (E; 5.00 g, 26.0 mmol) in anhydrous acetonitrile (17 mL) was added thionyl chloride (3.87 g, 32.5 mmol) at 0° C. The ice bath was removed and the resulting light yellow solution was stirred for 1 h. The reaction was analyzed by GC-MS, which confirmed full conversion of the starting material (SM) to the desired 5-(1-chloroethyl)-2-trifluoromethylpyrimidine intermediate ((E) m/z 210 (M)$^+$). The solvent and excess thionyl chloride were removed on the rotary evaporator, and the residual amber oil was dissolved in anhydrous acetonitrile (20 mL) and used without further purification.

B) The solution of 5-(1-chloroethyl)-2-trifluoromethylpyrimidine (F) was cooled to 0° C., and sodium thiomethoxide (2.96 g, 42.3 mmol) was added in portions (3×0.99 g) over 5 minutes (min). The ice bath was removed and the resulting orange mixture was warmed to RT and stirred for 1 h. The reaction was diluted with brine (100 mL) and extracted with Et$_2$O (3×150 mL). The organic extracts were combined, dried over Na$_2$SO$_4$, filtered, and concentrated to give an amber oil (5.21 g crude). The oil was purified by flash chromatography (330 g SiO$_2$, 0→100% EtOAc/hexanes gradient) to give 5-(1-methylsulfonylethyl)-2-trifluoromethylpyrimidine (G; 4.16 g, 72%) as a yellow oil: $^1$H NMR (300 MHz, CDCl$_3$) δ 8.86 (s, 2H), 3.92 (q, J=7.3, 1H), 1.98 (s, 3H), 1.68 (d, J=7.2, 3H); MS (EI) m/z 222 (M)$^+$.

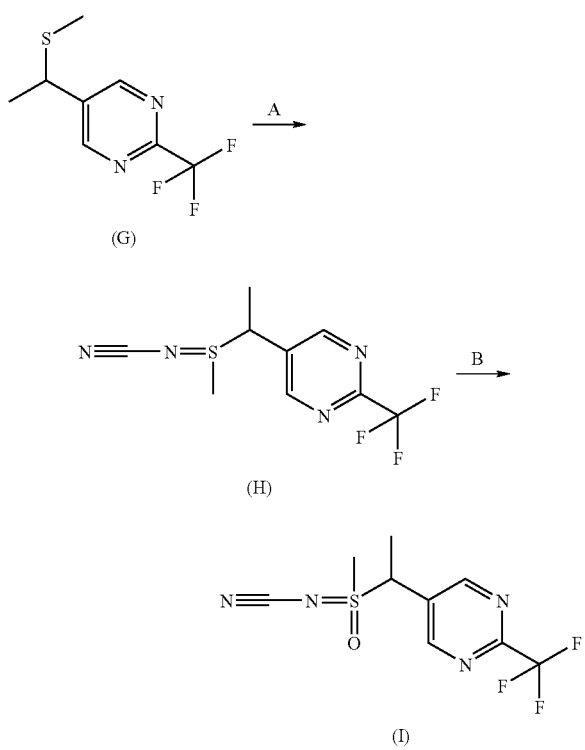

A) To a magnetically stirred solution of 5-(1-methylsulfonylethyl)-2-trifluoromethylpyrimidine (G; 0.50 g, 2.60 mmol) and cyanamide (0.114 g, 2.73 mmol) in anhydrous acetonitrile (5.2 mL) was added iodobenzenediacetate (0.924 g, 2.87 mmol) at 0° C. under nitrogen ($N_2$). The ice bath was removed, the pale yellow mixture was warmed to RT and the resulting orange solution was stirred for 16 h. The reaction was analyzed by LC-MS, which confirmed the formation of methyl{1-[2-(trifluoromethyl)pyrimidin-5-yl]ethyl}-$\lambda^4$-sulfanylidenecyanamide (H) ((ESI) m/z 263 [M+H]$^+$, 261 [M−H]$^−$). The solution was washed with hexanes (5×10 mL), and the acetonitrile was removed on the rotary evaporator to give an orange oil which was dissolved in $CH_2Cl_2$ (26 mL) and used without further purification.

B) To a magnetically stirred solution of methyl{1-[2-(trifluoromethyl)pyrimidin-5-yl]ethyl}-$\lambda^4$-sulfanylidenecyanamide (H; 0.68 g, 2.60 mmol) in $CH_2Cl_2$ (26 mL) was slowly added aqueous sodium permanganate ($NaMnO_4$) (0.92 g of 40%, 2.60 mmol) at 0° C. The ice bath was removed and the resulting dark mixture was warmed to RT and stirred for 1.5 h. The reaction was washed with aqueous sodium bisulfite, and the entire mixture was filtered. The phases were separated and the aqueous phase was extracted with $CH_2Cl_2$ (2×25 mL). The organic phases were combined, washed with brine (25 mL), dried over $Na_2SO_4$, filtered, and concentrated to give a white, pasty residue (0.517 g crude). The crude material was purified by flash chromatography (80 g $SiO_2$, 0→100% acetone/Hexanes gradient) to give a 1:1 mixture of diastereomers of methyl(oxido){1-[2-(trifluoromethyl)pyrimidin-5-yl]ethyl}-$\lambda^4$-sulfanylidenecyanamide (I; 0.33 g, 46%) as a colorless, waxy solid: $^1$H NMR (300 MHz, $CDCl_3$) δ 9.20 (d, J=1.3 Hz, 2H), 5.40 (q, J=7.1 Hz, 0.5H), 5.38 (q, J=7.1 Hz, 0.5H), 3.54 (s, 1.5H), 3.53 (s, 1.5H), 1.92 (d, J=7.1 Hz, 1.5H), 1.91 (d, J=7.0 Hz, 1.5H); MS (ESIMS) m/z 279 [M+H]$^+$, m/z 277 [M−H]$^−$.

Example IV

Insecticidal Testing

The compounds identified in the foregoing examples were tested against cotton aphid using procedures described hereinafter.

Insecticidal Test for Cotton Aphid (*Aphis gossypii*) in Foliar Spray Assay

Squash seedlings with fully expanded cotyledon leaves were trimmed to one cotyledon per plant and infested with cotton aphid (wingless adults and nymphs) 1 day prior to chemical application. Each plant was examined before chemical application to ensure uniform infestation (ca. 30-70 aphids per plant). Compounds (2 mg) were dissolved in 2 mL of acetone/methanol (1:1) solvent, forming stock solutions of 1000 ppm. The stock solutions were diluted 5× with 0.025% Tween 20 in $H_2O$ to obtain a solution at 200 ppm. A hand-held Devilbiss aspirator type sprayer was used to apply the spray solutions until runoff to both sides of the squash cotyledon leaves. Four plants (4 replications) were used for each compound. Reference plants (solvent check) were sprayed with the diluent only. Treated plants were held in a holding room for 3 days at approximately 23° C. and 40% relative humidity (RH) before the number of live aphids on each plant was recorded. Insecticidal activity was measured by Corrected % Control using Abbott's correction formula and presented in Table 1-Activity:

Corrected % Control=100*(X−Y)/X where X=No. of live aphids on solvent check plants
Y=No. of live aphids on treated plants
Results are shown in Table 1.

TABLE 1

| | Activity. |
|---|---|
| Comp # | % Control at ppm, against cotton aphid on squash (foliar spray) 200 ppm |
| 1 | A |
| 2 | A |
| 3 | A |

In each case of Table 1 the rating scale is as follows:

| % Control (or Mortality) | Rating |
|---|---|
| 80-100 | A |
| Less than 80 | B |
| Not tested | C |

Acid & Salt Derivatives, and Solvates

The compounds disclosed in this invention can be in the form of pesticidally acceptable acid addition salts.

By way of non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids.

Additionally, by way of non-limiting example, an acid function can form salts including those derived from alkali or alkaline earth metals and those derived from ammonia and amines. Examples of preferred cations include sodium, potassium, magnesium, and aminium cations.

The salts are prepared by contacting the free base form with a sufficient amount of the desired acid to produce a salt. The free base forms may be regenerated by treating the salt with a suitable dilute aqueous base solution such as dilute aqueous NaOH, potassium carbonate, ammonia, and sodium bicarbonate. As an example, in many cases, a pesticide is modified to a more water soluble form e.g. 2,4-dichlorophenoxy acetic acid dimethyl amine salt is a more water soluble form of 2,4-dichlorophenoxy acetic acid, a well known herbicide.

The compounds disclosed in this invention can also form stable complexes with solvent molecules that remain intact after the non-complexed solvent molecules are removed from the compounds. These complexes are often referred to as "solvates."

Stereoisomers

Certain compounds disclosed in this invention can exist as one or more stereoisomers. The various stereoisomers include geometric isomers, diastereomers, and enantiomers. Thus, the compounds disclosed in this invention include racemic mixtures, individual stereoisomers, and optically active mixtures. It will be appreciated by those skilled in the art that one stereoisomer may be more active than the others. Individual stereoisomers and optically active mixtures may be obtained by selective synthetic procedures, by conventional synthetic procedures using resolved starting materials, or by conventional resolution procedures.

Pests

In another embodiment, the invention disclosed in this document can be used to control pests.

In another embodiment, the invention disclosed in this document can be used to control pests of the Phylum Nematoda.

In another embodiment, the invention disclosed in this document can be used to control pests of the Phylum Arthropoda.

In another embodiment, the invention disclosed in this document can be used to control pests of the Subphylum Chelicerata.

In another embodiment, the invention disclosed in this document can be used to control pests of the Class Arachnida.

In another embodiment, the invention disclosed in this document can be used to control pests of the Subphylum Myriapoda.

In another embodiment, the invention disclosed in this document can be used to control pests of the Class Symphyla.

In another embodiment, the invention disclosed in this document can be used to control pests of the Subphylum Hexapoda.

In another embodiment, the invention disclosed in this document can be used to control pests of the Class Insecta.

In another embodiment, the invention disclosed in this document can be used to control Coleoptera (beetles). A non-exhaustive list of these pests includes, but is not limited to, *Acanthoscelides* spp. (weevils), *Acanthoscelides obtectus* (common bean weevil), *Agrilus planipennis* (emerald ash borer), *Agriotes* spp. (wireworms), *Anoplophora glabripennis* (Asian longhorned beetle), *Anthonomus* spp. (weevils), *Anthonomus grandis* (boll weevil), *Aphidius* spp., *Apion* spp. (weevils), *Apogonia* spp. (grubs), *Ataenius spretulus* (Black Turgrass Ataenius), *Atomaria linearis* (pygmy mangold beetle), *Aulacophore* spp., *Bothynoderes punctiventris* (beet root weevil), *Bruchus* spp. (weevils), *Bruchus pisorum* (pea weevil), *Cacoesia* spp., *Callosobruchus maculatus* (southern cow pea weevil), *Carpophilus hemipteras* (dried fruit beetle), *Cassida vittata*, *Cerostema* spp, *Cerotoma* spp. (chrysomeids), *Cerotoma trifurcata* (bean leaf beetle), *Ceutorhynchus* spp. (weevils), *Ceutorhynchus assimilis* (cabbage seedpod weevil), *Ceutorhynchus napi* (cabbage curculio), *Chaetocnema* spp. (chrysomelids), *Colaspis* spp. (soil beetles), *Conoderus scalaris*, *Conoderus stigmosus*, *Conotrachelus nenuphar* (plum curculio), *Cotinus nitidis* (Green June beetle), *Crioceris asparagi* (asparagus beetle), *Cryptolestes ferrugineus* (rusty grain beetle), *Cryptolestes pusillus* (flat grain beetle), *Cryptolestes turcicus* (Turkish grain beetle), *Ctenicera* spp. (wireworms), *Curculio* spp. (weevils), *Cyclocephala* spp. (grubs), *Cylindrocpturus adspersus* (sunflower stem weevil), *Deporaus marginatus* (mango leaf-cutting weevil), *Dermestes lardarius* (larder beetle), *Dermestes maculates* (hide beetle), *Diabrotica* spp. (chrysolemids), *Epilachna varivestis* (Mexican bean beetle), *Faustinus cubae*, *Hylobius pales* (pales weevil), *Hypera* spp. (weevils), *Hypera postica* (alfalfa weevil), *Hyperdoes* spp. (Hyperodes weevil), *Hypothenemus hampei* (coffee berry beetle), *Ips* spp. (engravers), *Lasioderma serricorne* (cigarette beetle), *Leptinotarsa decemlineata* (Colorado potato beetle), *Liogenys fuscus, Liogenys suturalis, Lissorhoptrus oryzophilus* (rice water weevil), *Lyctus* spp. (wood beetles/powder post beetles), *Maecolaspis joliveti, Megascelis* spp., *Melanotus communis, Meligethes* spp., *Meligethes aeneus* (blossom beetle), *Melolontha melolontha* (common European cockchafer), *Oberea brevis, Oberea linearis, Oryctes rhinoceros* (date palm beetle), *Oryzaephilus mercator* (merchant grain beetle), *Oryzaephilus surinamensis* (sawtoothed grain beetle), *Otiorhynchus* spp. (weevils), *Oulema melanopus* (cereal leaf beetle), *Oulema oryzae, Pantomorus* spp. (weevils), *Phyllophaga* spp. (May/June beetle), *Phyllophaga cuyabana, Phyllotreta* spp. (chrysomelids), *Phynchites* spp., *Popillia japonica* (Japanese beetle), *Prostephanus truncates* (larger grain borer), *Rhizopertha dominica* (lesser grain borer), *Rhizotrogus* spp. (European chafer), *Rhynchophorus* spp. (weevils), *Scolytus* spp. (wood beetles), *Shenophorus* spp. (billbug), *Sitona lineatus* (pea leaf weevil), *Sitophilus* spp. (grain weevils), *Sitophilus granaries* (granary weevil), *Sitophilus oryzae* (rice weevil), *Stegobium paniceum* (drugstore beetle), *Tribolium* spp. (flour beetles), *Tribolium castaneum* (red flour beetle), *Tribolium confusum* (confused flour beetle), *Trogoderma variabile* (warehouse beetle), and *Zabrus tenebioides*.

In another embodiment, the invention disclosed in this document can be used to control Dermaptera (earwigs).

In another embodiment, the invention disclosed in this document can be used to control Dictyoptera (cockroaches). A non-exhaustive list of these pests includes, but is not limited to, *Blattella germanica* (German cockroach), *Blatta orientalis* (oriental cockroach), *Parcoblatta pennylvanica, Periplaneta americana* (American cockroach), *Periplaneta australoasiae* (Australian cockroach), *Periplaneta brunnea* (brown cockroach), *Periplaneta fuliginosa* (smokybrown cockroach), *Pyncoselus suninamensis* (Surinam cockroach), and *Supella longipalpa* (brownbanded cockroach).

In another embodiment, the invention disclosed in this document can be used to control Diptera (true flies). A non-exhaustive list of these pests includes, but is not limited to, *Aedes* spp. (mosquitoes), *Agromyza frontella* (alfalfa blotch leafminer), *Agromyza* spp. (leaf miner flies), *Anastrepha* spp.

(fruit flies), *Anastrepha suspensa* (Caribbean fruit fly), *Anopheles* spp. (mosquitoes), *Batrocera* spp. (fruit flies), *Bactrocera cucurbitae* (melon fly), *Bactrocera dorsalis* (oriental fruit fly), *Ceratitis* spp. (fruit flies), *Ceratitis capitata* (Mediterranean fruit fly), *Chrysops* spp. (deer flies), *Cochliomyia* spp. (screwworms), *Contarinia* spp. (gall midges), *Culex* spp. (mosquitoes), *Dasineura* spp. (gall midges), *Dasineura brassicae* (cabbage gall midge), *Delia* spp., *Delia platura* (seedcorn maggot), *Drosophila* spp. (vinegar flies), *Fannia* spp. (filth flies), *Fannia canicularis* (little house fly), *Fannia scalaris* (latrine fly), *Gasterophilus intestinalis* (horse bot fly), *Gracillia perseae*, *Haematobia irritans* (horn fly), *Hylemyia* spp. (root maggots), *Hypoderma lineatum* (common cattle grub), *Liriomyza* spp. (leafminer flies), *Liriomyza brassica* (serpentine leafminer), *Melophagus ovinus* (sheep ked), *Musca* spp. (muscid flies), *Musca autumnalis* (face fly), *Musca domestica* (house fly), *Oestrus ovis* (sheep bot fly), *Oscinella frit* (frit fly), *Pegomyia betae* (beet leafminer), *Phorbia* spp., *Psila rosae* (carrot rust fly), *Rhagoletis cerasi* (cherry fruit fly), *Rhagoletis pomonella* (apple maggot), *Sitodiplosis mosellana* (orange wheat blossom midge), *Stomoxys calcitrans* (stable fly), *Tabanus* spp. (horse flies), and *Tipula* spp. (crane flies).

In another embodiment, the invention disclosed in this document can be used to control Hemiptera (true bugs). A non-exhaustive list of these pests includes, but is not limited to, *Acrostemum hilare* (green stink bug), *Blissus leucopterus* (chinch bug), *Calocoris norvegicus* (potato mirid), *Cimex hemipterus* (tropical bed bug), *Cimex lectularius* (bed bug), *Dagbertus fasciatus*, *Dichelops furcatus*, *Dysdercus suturellus* (cotton stainer), *Edessa meditabunda*, *Eurygaster maura* (cereal bug), *Euschistus heros*, *Euschistus servus* (brown stink bug), *Helopeltis antonii*, *Helopeltis theivora* (tea blight plantbug), *Lagynotomus* spp. (stink bugs), *Leptocorisa oratorius*, *Leptocorisa varicornis*, *Lygus* spp. (plant bugs), *Lygus hesperus* (western tarnished plant bug), *Maconellicoccus hirsutus*, *Neurocolpus longirostris*, *Nezara viridula* (southern green stink bug), *Phytocoris* spp. (plant bugs), *Phytocoris californicus*, *Phytocoris relativus*, *Piezodorus guildingi*, *Poecilocapsus lineatus* (fourlined plant bug), *Psallus vaccinicola*, *Pseudacysta perseae*, *Scaptocoris castanea*, and *Triatoma* spp. (bloodsucking conenose bugs/kissing bugs).

In another embodiment, the invention disclosed in this document can be used to control Homoptera (aphids, scales, whiteflies, leafhoppers). A non-exhaustive list of these pests includes, but is not limited to, *Acrythosiphon pisum* (pea aphid), *Adelges* spp. (adelgids), *Aleurodes proletella* (cabbage whitefly), *Aleurodicus disperses*, *Aleurothrixus floccosus* (woolly whitefly), *Aluacaspis* spp., *Amrasca bigutella bigutella*, *Aphrophora* spp. (leafhoppers), *Aonidiella aurantii* (California red scale), *Aphis* spp. (aphids), *Aphis gossypii* (cotton aphid), *Aphis pomi* (apple aphid), *Aulacorthum solani* (foxglove aphid), *Bemisia* spp. (whiteflies), *Bemisia argentifolii*, *Bemisia tabaci* (sweetpotato whitefly), *Brachycolus noxius* (Russian aphid), *Brachycorynella asparagi* (asparagus aphid), *Brevennia rehi*, *Brevicoryne brassicae* (cabbage aphid), *Ceroplastes* spp. (scales), *Ceroplastes rubens* (red wax scale), *Chionaspis* spp. (scales), *Chrysomphalus* spp. (scales), *Coccus* spp. (scales), *Dysaphis plantaginea* (rosy apple aphid), *Empoasca* spp. (leafhoppers), *Eriosoma lanigerum* (woolly apple aphid), *Icerya purchasi* (cottony cushion scale), *Idioscopus nitidulus* (mango leafhopper), *Laodelphax striatellus* (smaller brown planthopper), *Lepidosaphes* spp., *Macrosiphum* spp., *Macrosiphum euphorbiae* (potato aphid), *Macrosiphum granarium* (English grain aphid), *Macrosiphum rosae* (rose aphid), *Macrosteles quadrilineatus* (aster leafhopper), *Mahanarva frimbiolata*, *Metopolophium dirhodum* (rose grain aphid), *Mictis longicomis*, *Myzus persicae* (green peach aphid), *Nephotettix* spp. (leafhoppers), *Nephotettix cinctipes* (green leafhopper), *Nilaparvata lugens* (brown planthopper), *Parlatoria pergandii* (chaff scale), *Parlatoria ziziphi* (ebony scale), *Peregrinus maidis* (corn delphacid), *Philaenus* spp. (spittlebugs), *Phylloxera vitifoliae* (grape phylloxera), *Physokermes piceae* (spruce bud scale), *Planococcus* spp. (mealybugs), *Pseudococcus* spp. (mealybugs), *Pseudococcus brevipes* (pine apple mealybug), *Quadraspidiotus perniciosus* (San Jose scale), *Rhapalosiphum* spp. (aphids), *Rhapalosiphum maida* (corn leaf aphid), *Rhapalosiphum padi* (oat bird-cherry aphid), *Saissetia* spp. (scales), *Saissetia oleae* (black scale), *Schizaphis graminum* (greenbug), *Sitobion avenae* (English grain aphid), *Sogatella furcifera* (white-backed planthopper), *Therioaphis* spp. (aphids), *Toumeyella* spp. (scales), *Toxoptera* spp. (aphids), *Trialeurodes* spp. (whiteflies), *Trialeurodes vaporariorum* (greenhouse whitefly), *Trialeurodes abutiloneus* (banded-wing whitefly), *Unaspis* spp. (scales), *Unaspis yanonensis* (arrowhead scale), and *Zulia entreriana*.

In another embodiment, the invention disclosed in this document can be used to control Hymenoptera (ants, wasps, and bees). A non-exhaustive list of these pests includes, but is not limited to, *Acromyrrmex* spp., *Athalia rosae*, *Atta* spp. (leafcutting ants), *Camponotus* spp. (carpenter ants), *Diprion* spp. (sawflies), *Formica* spp. (ants), *Iridomyrmex humilis* (Argentine ant), *Monomorium* ssp., *Monomorium minumum* (little black ant), *Monomorium pharaonis* (Pharaoh ant), *Neodiprion* spp. (sawflies), *Pogonomyrmex* spp. (harvester ants), *Polistes* spp. (paper wasps), *Solenopsis* spp. (fire ants), *Tapoinoma sessile* (odorous house ant), *Tetranomorium* spp. (pavement ants), *Vespula* spp. (yellow jackets), and *Xylocopa* spp. (carpenter bees).

In another embodiment, the invention disclosed in this document can be used to control Isoptera (termites). A non-exhaustive list of these pests includes, but is not limited to, *Coptotermes* spp., *Coptotermes curvignathus*, *Coptotermes frenchii*, *Coptotermes formosanus* (Formosan subterranean termite), *Cornitermes* spp. (nasute termites), *Cryptotermes* spp. (drywood termites), *Heterotermes* spp. (desert subterranean termites), *Heterotermes aureus*, *Kalotermes* spp. (drywood termites), *Incistitermes* spp. (drywood termites), *Macrotermes* spp. (fungus growing termites), *Marginitermes* spp. (drywood termites), *Microcerotermes* spp. (harvester termites), *Microtermes obesi*, *Procornitermes* spp., *Reticulitermes* spp. (subterranean termites), *Reticulitermes banyulensis*, *Reticulitermes* grassei, *Reticulitermes flavipes* (eastern subterranean termite), *Reticulitermes hageni*, *Reticulitermes hesperus* (western subterranean termite), *Reticulitermes santonensis*, *Reticulitermes speratus*, *Reticulitermes tibialis*, *Reticulitermes virginicus*, *Schedorhinotermes* spp., and *Zootermopsis* spp. (rotten-wood termites).

In another embodiment, the invention disclosed in this document can be used to control Lepidoptera (moths and butterflies). A non-exhaustive list of these pests includes, but is not limited to, *Achoea janata*, *Adoxophyes* spp., *Adoxophyes orana*, *Agrotis* spp. (cutworms), *Agrotis ipsilon* (black cutworm), *Alabama argillacea* (cotton leafworm), *Amorbia cuneana*, *Amyelosis transitella* (navel orangeworm), *Anacamptodes defectaria*, *Anarsia lineatella* (peach twig borer), *Anomis sabulifera* (jute looper), *Anticarsia gemmatalis* (velvetbean caterpillar), *Archips argyrospila* (fruittree leafroller), *Archips rosana* (rose leaf roller), *Argyrotaenia* spp. (tortricid moths), *Argyrotaenia citrana* (orange tortrix), *Autographa gamma*, *Bonagota cranaodes*, *Borbo cinnara* (rice leaf folder), *Bucculatrix thurberiella* (cotton leafperforator), *Caloptilia* spp. (leaf miners), *Capua reticulana*, *Carposina*

*niponensis* (peach fruit moth), *Chilo* spp., *Chlumetia transversa* (mango shoot borer), *Choristoneura rosaceana* (oblique banded leafroller), *Chrysodeixis* spp., *Cnaphalocerus medinalis* (grass leafroller), *Colias* spp., *Conpomorpha cramerella, Cossus cossus* (carpenter moth), *Crambus* spp. (Sod webworms), *Cydia funebrana* (plum fruit moth), *Cydia molesta* (oriental fruit moth), *Cydia nignicana* (pea moth), *Cydia pomonella* (codling moth), *Darna diducta, Diaphania* spp. (stem borers), *Diatraea* spp. (stalk borers), *Diatraea saccharalis* (sugarcane borer), *Diatraea graniosella* (southwester corn borer), *Earias* spp. (bollworms), *Earias insulata* (Egyptian bollworm), *Earias vitella* (rough northern bollworm), *Ecdytopopha aurantianum, Elasmopalpus lignosellus* (lesser cornstalk borer), *Epiphysias postruttana* (light brown apple moth), *Ephestia* spp. (flour moths), *Ephestia cautella* (almond moth), *Ephestia elutella* (tobbaco moth), *Ephestia kuehniella* (Mediterranean flour moth), *Epimeces* spp., *Epinotia aporema, Erionota thrax* (banana skipper), *Eupoecilia ambiguella* (grape berry moth), *Euxoa auxiliaris* (army cutworm), *Feltia* spp. (cutworms), *Gortyna* spp. (stemborers), *Gracholita molesta* (oriental fruit moth), *Hedylepta indicata* (bean leaf webber), *Helicoverpa* spp. (noctuid moths), *Helicoverpa armigera* (cotton bollworm), *Helicoverpa zea* (bollworm/corn earworm), *Heliothis* spp. (noctuid moths), *Heliothis virescens* (tobacco budworm), *Hellula undalis* (cabbage webworm), *Indarbela* spp. (root borers), *Keiferia lycopersicella* (tomato pinworm), *Leucinodes orbonalis* (eggplant fruit borer), *Leucoptera malifoliella, Lithocollectis* spp., *Lobesia botrana* (grape fruit moth), *Loxagrotis* spp. (noctuid moths), *Loxagrotis albicosta* (western bean cutworm), *Lymantria dispar* (gypsy moth), *Lyonetia clerkella* (apple leaf miner), *Mahasena corbetti* (oil palm bagworm), *Malacosoma* spp. (tent caterpillars), *Mamestra brassicae* (cabbage armyworm), *Maruca testulalis* (bean pod borer), *Metisa plana* (bagworm), *Mythimna unipuncta* (true armyworm), *Neoleucinodes elegantalis* (small tomato borer), *Nymphula depunctalis* (rice caseworm), *Operophthera brumata* (winter moth), *Ostrinia nubilalis* (European corn borer), *Oxydia vesulia, Pandemis cerasana* (common currant tortrix), *Pandemis heparana* (brown apple tortrix), *Papilio demodocus, Pectinophora gossypiella* (pink bollworm), *Peridroma* spp. (cutworms), *Peridroma saucia* (variegated cutworm), *Perileucoptera coffeella* (white coffee leafminer), *Phthorimaea operculella* (potato tuber moth), *Phyllocnisitis citrella, Phyllonorycter* spp. (leafminers), *Pieris rapae* (imported cabbageworm), *Plathypena scabra, Plodia interpunctella* (Indian meal moth), *Plutella xylostella* (diamondback moth), *Polychrosis viteana* (grape berry moth), *Prays endocarpa, Prays oleae* (olive moth), *Pseudaletia* spp. (noctuid moths), *Pseudaletia unipunctata* (armyworm), *Pseudoplusia includens* (soybean looper), *Rachiplusia nu, Scirpophaga incertulas, Sesamia* spp. (stemborers), *Sesamia inferens* (pink rice stem borer), *Sesamia nonagrioides, Setora nitens, Sitotroga cerealella* (Angoumois grain moth), *Sparganothis pilleriana, Spodoptera* spp. (armyworms), *Spodoptera exigua* (beet armyworm), *Spodoptera fugiperda* (fall armyworm), *Spodoptera oridania* (southern armyworm), *Synanthedon* spp. (root borers), *Thecla basilides, Thermisia gemmatalis, Tineola bisselliella* (webbing clothes moth), *Trichoplusia ni* (cabbage looper), *Tuta absoluta, Yponomeuta* spp., *Zeuzera coffeae* (red branch borer), and *Zeuzera pyrina* (leopard moth).

In another embodiment, the invention disclosed in this document can be used to control Mallophaga (chewing lice). A non-exhaustive list of these pests includes, but is not limited to, *Bovicola ovis* (sheep biting louse), *Menacanthus stramineus* (chicken body louse), and *Menopon gallinea* (common hen louse).

In another embodiment, the invention disclosed in this document can be used to control Orthoptera (grasshoppers, locusts, and crickets). A non-exhaustive list of these pests includes, but is not limited to, *Anabrus simplex* (Mormon cricket), *Gryllotalpidae* (mole crickets), *Locusta migratoria, Melanoplus* spp. (grasshoppers), *Microcentrum retinerve* (angular winged katydid), *Pterophylla* spp. (katydids), *chistocerca gregaria, Scudderia furcata* (forktailed bush katydid), and *Valanga nigricorni*.

In another embodiment, the invention disclosed in this document can be used to control Phthiraptera (sucking lice). A non-exhaustive list of these pests includes, but is not limited to, *Haematopinus* spp. (cattle and hog lice), *Linognathus ovillus* (sheep louse), *Pediculus humanus capitis* (human body louse), *Pediculus humanus humanus* (human body lice), and *Pthirus pubis* (crab louse), In another embodiment, the invention disclosed in this document can be used to control Siphonaptera (fleas). A non-exhaustive list of these pests includes, but is not limited to, *Ctenocephalides canis* (dog flea), *Ctenocephalides felis* (cat flea), and *Pulex irritans* (human flea).

In another embodiment, the invention disclosed in this document can be used to control Thysanoptera (thrips). A non-exhaustive list of these pests includes, but is not limited to, *Frankliniella fusca* (tobacco thrips), *Frankliniella occidentalis* (western flower thrips), *Frankliniella shultzei Frankliniella williamsi* (corn thrips), *Heliothrips haemorrhaidalis* (greenhouse thrips), *Riphiphorothrips cruentatus, Scirtothrips* spp., *Scirtothrips citri* (citrus thrips), *Scirtothrips dorsalis* (yellow tea thrips), *Taeniothrips rhopalantennalis*, and *Thrips* spp.

In another embodiment, the invention disclosed in this document can be used to control Thysanura (bristletails). A non-exhaustive list of these pests includes, but is not limited to, *Lepisma* spp. (silverfish) and *Thermobia* spp. (firebrats).

In another embodiment, the invention disclosed in this document can be used to control Acarina (mites and ticks). A non-exhaustive list of these pests includes, but is not limited to, *Acarapsis woodi* (tracheal mite of honeybees), *Acarus* spp. (food mites), *Acarus siro* (grain mite), *Aceria mangiferae* (mango bud mite), *Aculops* spp., *Aculops lycopersici* (tomato russet mite), *Aculops pelekasi, Aculus pelekassi, Aculus schlechtendali* (apple rust mite), *Amblyomma americanum* (lone star tick), *Boophilus* spp. (ticks), *Brevipalpus obovatus* (privet mite), *Brevipalpus phoenicis* (red and black flat mite), *Demodex* spp. (mange mites), *Dermacentor* spp. (hard ticks), *Dermacentor variabilis* (American dog tick), *Dermatophagoides pteronyssinus* (house dust mite), *Eotetranycus* spp., *Eotetranychus carpini* (yellow spider mite), *Epitimerus* spp., *Eriophyes* spp., *Ixodes* spp. (ticks), *Metatetranycus* spp., *Notoedres cati, Oligonychus* spp., *Oligonychus coffee, Oligonychus ilicus* (southern red mite), *Panonychus* spp., *Panonychus citri* (citrus red mite), *Panonychus ulmi* (European red mite), *Phyllocoptruta oleivora* (citrus rust mite), *Polyphagotarsonemun latus* (broad mite), *Rhipicephalus sanguineus* (brown dog tick), *Rhizoglyphus* spp. (bulb mites), *Sarcoptes scabiei* (itch mite), *Tegolophus perseaflorae, Tetranychus* spp., *Tetranychus urticae* (two-spotted spider mite), and *Varroa destructor* (honey bee mite).

In another embodiment, the invention disclosed in this document can be used to control Nematoda (nematodes). A non-exhaustive list of these pests includes, but is not limited to, *Aphelenchoides* spp. (bud and leaf & pine wood nematodes), *Belonolaimus* spp. (sting nematodes), *Criconemella* spp. (ring nematodes), *Dirofilaria immitis* (dog heartwom), *Ditylenchus* spp. (stem and bulb nematodes), *Heterodera* spp. (cyst nematodes), *Heterodera zeae* (corn cyst nematode), *Hirschmanniella* spp. (root nematodes), *Hoplolaimus* spp. (lance nematodes), *Meloidogyne* spp. (root knot nematodes), *Meloidogyne incognita* (root knot nematode), *Onchocerca volvulus* (hook-tail worm), *Pratylenchus* spp. (lesion nematodes), *Radopholus* spp. (burrowing nematodes), and *Rotylenchus reniformis* (kidney-shaped nematode).

In another embodiment, the invention disclosed in this document can be used to control Symphyla (symphylans). A non-exhaustive list of these pests includes, but is not limited to, *Scutigerella immaculata*.

For more detailed information consult "Handbook of Pest Control—The Behavior, Life History, and Control of Household Pests" by Arnold Mallis, 9th Edition, copyright 2004 by GIE Media Inc.

Mixtures

Some of the pesticides that can be employed beneficially in combination with the invention disclosed in this document include, but are not limited to the following, 1,2-dichloropropane, 1,3-dichloropropene, abamectin, acephate, acequinocyl, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, amidithion, amidoflumet, aminocarb, amiton, amitraz, anabasine, arsenous oxide, athidathion, azadirachtin, azamethiphos, azinphos-ethyl, azinphos-methyl, azobenzene, azocyclotin, azothoate, barium hexafluorosilicate, barthrin, benclothiaz, bendiocarb, benfuracarb, benomyl, benoxafos, bensultap, benzoximate, benzyl benzoate, beta-cyfluthrin, beta-cypermethrin, bifenazate, bifenthrin, binapacryl, bioallethrin, bioethanomethrin, biopermethrin, bistrifluoron, borax, boric acid, bromfenvinfos, bromo-DDT, bromocyclen, bromophos, bromophos-ethyl, bromopropylate, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, chinomethionat, chlorantraniliprole, chlorbenside, chlorbicyclen, chlordane, chlordecone, chlordimeform, chlorethoxyfos, chlorfenapyr, chlorfenethol, chlorfenson, chlorfensulphide, chlorfenvinphos, chlorfluazuron, chlormephos, chlorobenzilate, chloroform, chloromebuform, chloromethiuron, chloropicrin, chloropropylate, chlorphoxim, chlorprazophos, chlorpyrifos, chlorpyrifos-methyl, chlorthiophos, chromafenozide, cinerin I, cinerin II, cismethrin, cloethocarb, clofentezine, closantel, clothianidin, copper acetoarsenite, copper arsenate, copper naphthenate, copper oleate, coumaphos, coumithoate, crotamiton, crotoxyphos, cruentaren A&B, crufomate, cryolite, cyanofenphos, cyanophos, cyanthoate, cyclethrin, cycloprothrin, cyenopyrafen, cyflumetofen, cyfluthrin, cyhalothrin, cyhexatin, cypermethrin, cyphenothrin, cyromazine, cythioate, d-limonene, dazomet, DBCP, DCIP, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diamidafos, diazinon, dicapthon, dichlofenthion, dichlofluanid, dichlorvos, dicofol, dicresyl, dicrotophos, dicyclanil, dieldrin, dienochlor, diflovidazin, diflubenzuron, dilor, dimefluthrin, dimefox, dimetan, dimethoate, dimethrin, dimethylvinphos, dimetilan, dinex, dinobuton, dinocap, dinocap-4, dinocap-6, dinocton, dinopenton, dinoprop, dinosam, dinosulfon, dinotefuran, dinoterbon, diofenolan, dioxabenzofos, dioxacarb, dioxathion, diphenyl sulfone, disulfuram, disulfoton, dithicrofos, DNOC, dofenapyn, doramectin, ecdysterone, emamectin, EMPC, empenthrin, endosulfan, endothion, endrin, EPN, epofenonane, eprinomectin, esfenvalerate, etaphos, ethiofencarb, ethion, ethiprole, ethoatemethyl, ethoprophos, ethyl-DDD, ethyl formate, ethylene dibromide, ethylene dichloride, ethylene oxide, etofenprox, etoxazole, etrimfos, EXD, famphur, fenamiphos, fenazaflor, fenazaquin, fenbutatin oxide, fenchlorphos, fenethacarb, fenfluthrin, fenitrothion, fenobucarb, fenothiocarb, fenoxacrim, fenoxycarb, fenpirithrin, fenpropathrin, fenpyroximate, fenson, fensulfothion, fenthion, fenthion-ethyl, fentrifanil, fenvalerate, fipronil, flonicamid, fluacrypyrim, fluazuron, flubendiamide, flubenzimine, flucofuron, flucycloxuron, flucythrinate, fluenetil, flufenerim, flufenoxuron, flufenprox, flumethrin, fluorbenside, fluvalinate, fonofos, formetanate, formothion, formparanate, fosmethilan, fospirate, fosthiazate, fosthietan, furathiocarb, furethrin, furfural, gamma-cyhalothrin, gamma-HCH, halfenprox, halofenozide, HCH, HEOD, heptachlor, heptenophos, heterophos, hexaflumuron, hexythiazox, HHDN, hydramethylnon, hydrogen cyanide, hydroprene, hyquincarb, imicyafos, imidacloprid, imiprothrin, indoxacarb, iodomethane, IPSP, isamidofos, isazofos, isobenzan, isocarbophos, isodrin, isofenphos, isoprocarb, isoprothiolane, isothioate, isoxathion, ivermectin jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfen, mesulfenfos, metaflumizone, metam, methacrifos, methamidophos, methidathion, methiocarb, methocrotophos, methomyl, methoprene, methoxychlor, methoxyfenozide, methyl bromide, methylchloroform, methylene chloride, methyl isothiocyanate, metofluthrin, metolcarb, metoxadiazone, mevinphos, mexacarbate, milbemectin, milbemycin oxime, mipafox, mirex, MNAF, monocrotophos, morphothion, moxidectin, naftalofos, naled, naphthalene, nicotine, nifluridide, nikkomycins, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phosphocarb, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, proclonol, profenofos, profluthrin, promacyl, promecarb, propaphos, propargite, propetamphos, propoxur, prothidathion, prothiofos, prothoate, protrifenbute, pyraclofos, pyrafluprole, pyrazophos, pyresmethrin, pyrethrin I, pyrethrin II, pyridaben, pyridalyl, pyridaphenthion, pyrifluquinazon, pyrimidifen, pyrimitate, pyriprole, pyriproxyfen, quassia, quinalphos, quinalphos-methyl, quinothion, quantiofos, rafoxanide, resmethrin, rotenone, ryania, sabadilla, schradan, selamectin, silafluofen, sodium arsenite, sodium fluoride, sodium hexafluorosilicate, sodium thiocyanate, sophamide, spinetoram, spinosad, spirodiclofen, spiromesifen, spirotetramat, sulcofuron, sulfuram, sulfluramid, sulfotep, sulfur, sulfuryl fluoride, sulprofos, tau fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetradifon, tetramethrin, tetranactin, tetrasul, theta cypermethrin, thiacloprid, thiamethoxam, thicrofos, thiocarboxime, thiocyclam, thiodicarb, thiofanox, thiometon, thionazin, thioquinox, thiosultap, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin and zolaprofos.

Additionally, any combination of the above pesticides can be used.

The invention disclosed in this document can also be used with herbicides and fungicides, or both for reasons of economy and synergy.

The invention disclosed in this document can be used with antimicrobials, bactericides, defoliants, safeners, synergists, algaecides, attractants, desiccants, pheromones, repellants, animal dips, avicides, disinfectants, semiochemicals, and molluscicides (these categories not necessarily mutually exclusive) for reasons of economy, and synergy.

For more information consult "Compendium of Pesticide Common Names" located at http://www.alanwood.net/pesticides/index.html as of the filing date of this document. Also consult "The Pesticide Manual" 14th Edition, edited by C D S Tomlin, copyright 2006 by British Crop Production Council.

Synergistic Mixtures

The invention disclosed in this document can be used with other compounds such as the ones mentioned under the heading "Mixtures" to form synergistic mixtures where the mode of action of the compounds in the mixtures are the same, similar, or different.

Examples of mode of actions include, but are not limited to: acetylcholinesterase inhibitor; sodium channel modulator; chitin biosynthesis inhibitor; GABA-gated chloride channel antagonist; GABA- and glutamate-gated chloride channel agonist; acetylcholine receptor agonist; MET I inhibitor; Mg-stimulated ATPase inhibitor; nicotinic acetylcholine receptor; Midgut membrane disrupter; and oxidative phosphorylation disrupter.

Additionally, the following compounds are known as synergists and can be used with the invention disclosed in this document: piperonyl butoxide, piprotal, propyl isome, sesamex, sesamolin, and sulfoxide.

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions.

For further information on formulation types see "Catalogue of pesticide formulation types and international coding system" Technical Monograph n°2, 5th Edition by CropLife International (2002).

Pesticides are applied most often as aqueous suspensions or emulsions prepared from concentrated formulations of such pesticides. Such water-soluble, water-suspendable, or emulsifiable formulations, are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and nonionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and nonionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums, may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They are used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, the invention disclosed in this document when used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, antifoam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of a particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Nonionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The type of surfactants usually used for solubilization are nonionics: sorbitan monooleates; sorbitan monooleate ethoxylates; and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often nonionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, Ultra low volume formulations, and to a lesser extent granular formulations. Sometimes mixtures of solvents are used. The first main groups of solvents are aliphatic paraffinic oils such as kerosene or refined paraffins. The second main group and the most common comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are limited to, montmorillonite, e.g. bentonite; magnesium aluminum silicate; and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazalin-3-one (BIT).

The presence of surfactants, which lower interfacial tension, often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane while the non-silicone anti-foam agents are water-insoluble oils, such as octanol and nonanol, or silica. In both cases, the function of the anti-foam agent is to displace the surfactant from the air-water interface.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Applications

The actual amount of pesticide to be applied to loci of pests is generally not critical and can readily be determined by those skilled in the art. In general, concentrations from about 0.01 grams of pesticide per hectare to about 5000 grams of pesticide per hectare are expected to provide good control.

The locus to which a pesticide is applied can be any locus inhabited by an pest, for example, vegetable crops, fruit and nut trees, grape vines, ornamental plants, domesticated animals, the interior or exterior surfaces of buildings, and the soil around buildings. Controlling pests generally means that pest populations, activity, or both, are reduced in a locus. This can come about when: pest populations are repulsed from a locus; when pests are incapacitated, partially or completely, temporarily or permanently, in or around a locus; or pests are exterminated, in whole or in part, in or around a locus. Of course a combination of these results can occur. Generally, pest populations, activity, or both are desirably reduced more than fifty percent, preferably more than 90 percent, even more preferably 99 percent.

Generally, with baits, the baits are placed in the ground where, for example, termites can come into contact with the bait. Baits can also be applied to a surface of a building, (horizontal, vertical, or slant surface) where, for example, ants, termites, cockroaches, and flies, can come into contact with the bait.

Because of the unique ability of the eggs of some pests to resist pesticides repeated applications may be desirable to control newly emerged larvae.

Systemic movement of pesticides in plants may be utilized to control pests on one portion of the plant by applying the pesticides to a different portion of the plant, or to a location where the root system of a plant can uptake pesticides. For example, control of foliar-feeding insects can be controlled by drip irrigation or furrow application, or by treating the seed before planting. Seed treatment can be applied to all types of seeds, including those from which plants genetically transformed to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement or any other beneficial traits. Furthermore, such seed treatments with the invention disclosed in this document can further enhance the ability of a plant to better withstand stressful growing conditions. This results in a healthier, more vigorous plant, which can lead to higher yields at harvest time.

It should be readily apparent that the invention can be used with plants genetically transformed to express specialized traits, such as *Bacillus thuringiensis* or other insecticidal toxins, or those expressing herbicide resistance, or those with "stacked" foreign genes expressing insecticidal toxins, herbicide resistance, nutrition-enhancement or any other beneficial traits. An example of such a use is spraying such plants with the invention disclosed in this document.

The invention disclosed in this document is suitable for controlling endoparasites and ectoparasites in the veterinary medicine sector or in the field of animal keeping. Compounds according to the invention are applied here in a known manner, such as by oral administration in the form of, for example, tablets, capsules, drinks, granules, by dermal application in the form of, for example, dipping, spraying, pouring on, spotting on, and dusting, and by parenteral administration in the form of, for example, an injection.

The invention disclosed in this document can also be employed advantageously in livestock keeping, for example, cattle, sheep, pigs, chickens, and geese. Suitable formulations are administered orally to the animals with the drinking water or feed. The dosages and formulations that are suitable depend on the species.

Before a pesticide can be used or sold commercially, such pesticide undergoes lengthy evaluation processes by various governmental authorities (local, regional, state, national, international). Voluminous data requirements are specified by regulatory authorities and must be addressed through data generation and submission by the product registrant or by another on the product registrant's behalf. These governmental authorities then review such data and if a determination of safety is concluded, provide the potential user or seller with product registration approval. Thereafter, in that locality where the product registration is granted and supported, such user or seller may use or sell such pesticide.

What is claimed is:

1. A composition comprising a compound having the following general formula:

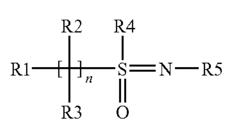

wherein

R1 is (a) an unsubstituted pyrimidinyl, pyridazinyl, or pyrazinyl, or (b) a substituted pyrimidinyl, pyridazinyl or pyrazinyl, wherein each substituted pyrimidinyl, pyridazinyl, or pyrazinyl, has one or more substituents independently selected from ($C_2$-$C_6$)alkenyl, ($C_2$-$C_6$)alkenyloxy, ($C_1$-$C_6$)alkoxy, ($C_1$-$C_6$)alkyl, ($C_2$-$C_6$)alkynyl, ($C_2$-$C_6$)alkynyloxy, aryl, ($C_3$-$C_6$)cycloalkenyl, ($C_3$-$C_6$)cycloalkenyloxy, ($C_3$-$C_6$)cycloalkyl, ($C_3$-$C_6$)cycloalkoxy, halo, halo($C_1$-$C_6$)alkyl, or heterocyclyl;

R2 is H, ($C_2$-$C_6$)alkenyl, ($C_2$-$C_6$)alkenyloxy, ($C_1$-$C_6$)alkoxy, ($C_1$-$C_6$)alkyl, ($C_2$-$C_6$)alkynyl, ($C_2$-$C_6$)alkynyloxy, aryl, ($C_3$-$C_6$)cycloalkenyl, ($C_3$-$C_6$)cycloalkenyloxy, ($C_3$-$C_6$)cycloalkyl, ($C_3$-$C_6$)cycloalkoxy, halo, halo($C_1$-$C_6$)alkyl, or heterocyclyl;

R3 is H, ($C_2$-$C_6$)alkenyl, ($C_2$-$C_6$)alkenyloxy, ($C_1$-$C_6$)alkoxy, ($C_1$-$C_6$)alkyl, ($C_2$-$C_6$)alkynyl, ($C_2$-$C_6$)alkynyloxy, aryl, ($C_3$-$C_6$)cycloalkenyl, ($C_3$-$C_6$)cycloalkenyloxy, ($C_3$-$C_6$)cycloalkyl, ($C_3$-$C_6$)cycloalkoxy, halo, halo($C_1$-$C_6$)alkyl, or heterocyclyl;

Optionally, R2 and R3 may form a ring wherein the ring contains 3 or more ring atoms optionally containing an O, S, or N atom;

R4 is H, ($C_2$-$C_6$)alkenyl, ($C_2$-$C_6$)alkenyloxy, ($C_1$-$C_6$)alkoxy, ($C_1$-$C_6$)alkyl, ($C_2$-$C_6$)alkynyl, ($C_2$-$C_6$)alkynyloxy, aryl, ($C_3$-$C_6$)cycloalkenyl, ($C_3$-$C_6$)cycloalkenyloxy, ($C_3$-$C_6$)cycloalkyl, ($C_3$-$C_6$)cycloalkoxy, halo, halo($C_1$-$C_6$)alkyl, or heterocyclyl;

Optionally, R4 and R2 are joined together to form a 4-, 5-, or 6-membered ring with $-(CH_2)-$;

R5 is $NO_2$, CN, $CO_2R_6$, unsubstituted heterocyclyl, substituted heterocyclyl, C(=(O or S))J(J1)(J2), wherein the substituted heterocyclyl has one or more substituents that are independently selected from ($C_2$-$C_6$)alkenyl, ($C_2$-$C_6$)alkenyloxy, ($C_1$-$C_6$)alkoxy, ($C_1$-$C_6$)alkyl, ($C_2$-$C_6$)alkynyl, ($C_2$-$C_6$)alkynyloxy, aryl, aryl($C_1$-$C_6$)alkyl, ($C_3$-$C_6$)cycloalkenyl, ($C_3$-$C_6$)cycloalkenyloxy, ($C_3$-$C_6$)cycloalkyl, ($C_3$-$C_6$)cycloalkoxy, halo, halo($C_1$-$C_6$)alkyl, heterocyclyl, and wherein J is N or C(J3), and wherein J1, J2, and J3, are independently selected from ($C_2$-$C_6$)alkenyl, ($C_2$-$C_6$)alkenyloxy, ($C_2$-$C_6$)alkenylthio, ($C_1$-$C_6$)alkoxy, ($C_1$-$C_6$)alkyl, ($C_1$-$C_6$)alkylthio, ($C_2$-$C_6$)alkynyl, ($C_2$-$C_6$)alkynyloxy, ($C_2$-$C_6$)alkynylthio, aryl, ($C_3$-$C_6$)cycloalkenyl, ($C_3$-$C_6$)cycloalkenyloxy, ($C_3$-$C_6$)cycloalkenylthio, ($C_3$-$C_6$)cycloalkyl, ($C_3$-$C_6$)cycloalkoxy, ($C_3$-$C_6$)cycloalkylthio, H, heterocyclyl, or ($C_0$-$C_6$)alkyl-C(=O)O(J4), wherein each of which may be independently substituted (except for H) with one or more of the following substituents, F, Cl, Br, I, CN, $NO_2$, ($C_1$-$C_6$)alkyl, ($C_2$-$C_6$)alkenyl, ($C_2$-$C_6$)alkynyl, ($C_1$-$C_6$)alkoxy, ($C_1$-$C_6$)haloalkyl, ($C_1$-$C_6$)haloalkoxy, halo($C_1$-$C_6$)alkylthio, $S(=O)_{n1}$(C1-$C_6$)alkyl (where n1=0-2), $S(=O)_{n2}$halo($C_1$-$C_6$)alkyl (where n2=0-2), $OSO_2$halo($C_1$-$C_6$)alkyl, C(=O)O($C_1$-$C_6$)alkyl, C(=O)($C_1$-$C_6$)alkyl, C(=O)halo($C_1$-$C_6$)alkyl, aryl, hydroxy($C_1$-$C_6$)alkyl, N(J5)(J6), and heterocyclyl, and wherein J1 and J2 may also form a 4-, 5-, or 6-membered ring, and wherein J4, J5, and J6 are independently selected from ($C_2$-$C_6$)alkenyl, ($C_2$-$C_6$)alkenyloxy, ($C_2$-$C_6$)alkenylthio, ($C_1$-$C_6$)alkoxy, ($C_1$-$C_6$)alkyl, ($C_1$-$C_6$)alkylthio, ($C_2$-$C_6$)alkynyl, ($C_2$-$C_6$)alkynyloxy, ($C_2$-$C_6$)alkynylthio, aryl, ($C_3$-$C_6$)cycloalkenyl, ($C_3$-$C_6$)cycloalkenyloxy, ($C_3$-$C_6$)cycloalkenylthio, ($C_3$-$C_6$)cycloalkyl, ($C_3$-$C_6$)cycloalkoxy, ($C_3$-$C_6$)cycloalkylthio, H, or heterocyclyl, and wherein R6=($C_1$-$C_3$)alkyl; and n is 0, 1, 2, or 3.

2. A composition according to claim 1 wherein R1 is 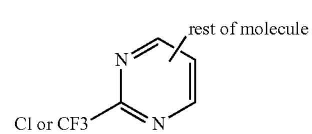 or 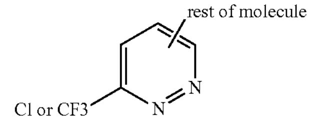 or

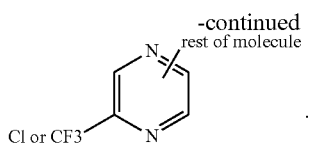

3. A composition according to claim 1, wherein R1 is a substituted pyrimidinyl, pyridazinyl, or pyrazinyl, wherein each substituted pyrimidinyl, pyridazinyl, or pyrazinyl, has one or more substituents independently selected from halo and halo($C_1$-$C_6$)alkyl.

4. A composition according to claim 1, wherein R2 is H or ($C_1$-$C_6$)alkyl.

5. A composition according to claim 1, wherein R3 is H or ($C_1$-$C_6$)alkyl.

6. A composition according to claim 1, wherein R4 is H or ($C_1$-$C_6$)alkyl.

7. A composition according to claim 1, wherein R5 is $NO_2$ or CN.

8. A composition according to claim 1, wherein R1 is a substituted pyrimidinyl, pyridazinyl, or pyrazinyl, wherein each substituted pyrimidinyl, pyridazinyl, or pyrazinyl, has one or more substituents independently selected from halo and halo($C_1$-$C_6$)alkyl;

R2 is H or ($C_1$-$C_6$)alkyl;

R3 is H or ($C_1$-$C_6$)alkyl;

R4 is H or ($C_1$-$C_6$)alkyl;

R5 is $NO_2$ or CN; and

N is 0, 1, 2, or 3.

9. A composition comprising a compound having the following formula

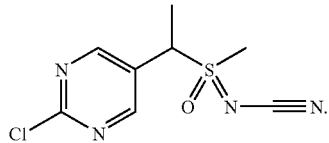

10. A composition comprising a compound having the following formula (2)

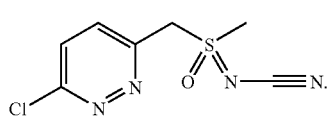

11. A composition comprising a compound having the following formula (3)

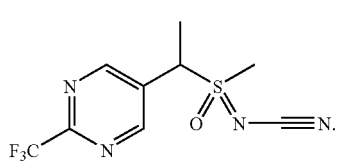

* * * * *